United States Patent
Erlen et al.

(10) Patent No.: US 12,118,261 B2
(45) Date of Patent: Oct. 15, 2024

(54) SAFETY-RELEVANT USER INTERFACE THAT DIRECTS INPUTS TO SAFE NUMERICAL VALUES

(71) Applicant: B. Braun Melsungen AG, Melsungen (DE)

(72) Inventors: Christoph Erlen, Kassel (DE); James Richard Green, Chester (GB); Mike Hoellerich, Cologne (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 17/800,952

(22) PCT Filed: Feb. 19, 2021

(86) PCT No.: PCT/EP2021/054114
§ 371 (c)(1),
(2) Date: Aug. 19, 2022

(87) PCT Pub. No.: WO2021/165449
PCT Pub. Date: Aug. 26, 2021

(65) Prior Publication Data
US 2023/0074811 A1    Mar. 9, 2023

(30) Foreign Application Priority Data
Feb. 21, 2020 (DE) .................. 10 2020 104 665.0

(51) Int. Cl.
*G06F 3/14* (2006.01)
*G06F 3/04886* (2022.01)

(52) U.S. Cl.
CPC ........ *G06F 3/1407* (2013.01); *G06F 3/04886* (2013.01)

(58) Field of Classification Search
None
See application file for complete search history.

(56) References Cited

U.S. PATENT DOCUMENTS 4,696,671 A * 9/1987 Epstein ................. A61M 5/172
128/DIG. 13
4,898,578 A 2/1990 Rubalcaba, Jr.
(Continued)

FOREIGN PATENT DOCUMENTS

JP 56087133 A * 7/1981
WO 2016205051 A1 12/2016

OTHER PUBLICATIONS

YouTube Video: "Perfusor Space: How to Operate", https://www.youtube.com/watch?v=kfiP2EALgzM, May 25, 2017, pp. 1-3 (Year: 2017).*

(Continued)

Primary Examiner — Kirk W Hermann
(74) Attorney, Agent, or Firm — Christopher A. Rothe; CM Law

(57) ABSTRACT

An apparatus for a safety-relevant application and a method for operating the apparatus. The apparatus has a user interface to display digits. The digits are intended to be filled with numerical values by a user. The user interface is designed to limit a selection of digits available for a user input when a numerical value is input by the user, for example the user's first input, for one of the digits that are to be filled.

18 Claims, 3 Drawing Sheets

(56) References Cited

U.S. PATENT DOCUMENTS

| | | | | |
|---|---|---|---|---|
| 5,428,805 | A * | 6/1995 | Morgan | G06F 15/0225<br>345/173 |
| 2004/0158193 | A1* | 8/2004 | Bui | A61M 5/172<br>128/DIG. 13 |
| 2006/0258985 | A1* | 11/2006 | Russell | G16H 40/67<br>604/151 |
| 2008/0126969 | A1* | 5/2008 | Blomquist | A61M 5/142<br>715/771 |
| 2014/0180711 | A1* | 6/2014 | Kamen | G06Q 10/10<br>705/2 |
| 2014/0283142 | A1* | 9/2014 | Shepherd | G06F 3/04817<br>726/30 |
| 2015/0142457 | A1* | 5/2015 | Marshall | G16H 50/50<br>705/2 |
| 2016/0015894 | A1* | 1/2016 | Murphy | G16H 70/20<br>604/506 |
| 2016/0370911 | A1* | 12/2016 | Tanenbaum | G06F 3/0416 |
| 2021/0170101 | A1* | 6/2021 | Cavendish, Jr. | G16H 10/60 |

OTHER PUBLICATIONS

Brian K Fung, B Braun Perfusor Training Video, Jan. 21, 2015, Youtube.com, https://www.youtube.com/watch?v=bqnhg_mvpS0 (Year: 2015).*

Search Report received in German Application No. 10 2020 104 665.0 dated Nov. 2, 2020, with translation, 18 pages.

Search Report received in International Application No. PCT/EP2021/054114 dated Apr. 30, 2021, with translation, 5 pages.

Written Opinion received in International Application No. PCT/EP2021/054114 dated Apr. 30, 2021, with translation, 11 pages.

YouTube Video: "Einweisung Perfusor Space," screen images, https://www.youtube.com/watch?v=QXibQbcYCU, Jun. 21, 2018, 2 pages.

* cited by examiner

![Fig. 7]

Flow rate
Delete | _ | _ | 2 | 0 . _ | _ | mL/h
Calculated Infusion Time= 2h 30 min
Back | Confirm

Fig. 7

⇧ Flow rate     DimenhyDRINATE 20 mg/250mL
0 mg/h    40
Delete | _ | _ | 5 | 0 . _ | _ | mg/h
Calculated Flow Rate =620 mL/h
Back | Limit Info | Other unit | Confirm

Fig. 8

⇧ Flow rate 0 mg/h     DimenhyDRINATE 20 mg/250mL
40     65

SOFT LIMIT WARNING!
Your value 50mg/h violates the soft limit of 40 mg/h

⇧ Overwrite | Other flow rate

Fig. 9

SAFETY-RELEVANT USER INTERFACE THAT DIRECTS INPUTS TO SAFE NUMERICAL VALUES

CROSS-REFERENCE TO RELATED APPLICATIONS

This application is the United States national stage entry of International Application No. PCT/EP2021/054114, filed Feb. 19, 2021, and claims priority to German Application No. 10 2020 104 665.0, filed Feb. 21, 2020. The contents of International Application No. PCT/EP2021/054114 and German Application No. 10 2020 104 665.0 are incorporated by reference herein in their entireties.

FIELD

The invention relates to safety-relevant, preferably medical applications, in particular to an apparatus for a safety-relevant, preferably medical application and to a method for operating such apparatus.

BACKGROUND

From the state of the art already a plurality of medical products is known which requires users, such as nursing staff and physicians, to input numerical values to user interfaces as part of a user interface of a medical apparatus. In many cases, the data or parameters input are safety-critical, in this case also referred to a safety-relevant, which means that an incorrect input may result or results in risks for the patient, the operator or others.

In the case of safety-critical apparatuses, such as an infusion pump, the flow volume is an example of a safety-critical parameter. A wrong input of the flow volume may result in wrong dosage. Depending on the drug infused, thus may cause serious harm to the patient.

However, the drawback of the state of the art always is the fact that the emphasis is placed on user friendliness rather than on maximum safety.

There is a need to provide concepts for increasing the safety level in safety-relevant applications, particularly in those where numerical values can be input by the operator.

SUMMARY

Hence, it is the object of the invention to avoid or at least to mitigate the drawbacks of the state of the art. In particular, the safety level when inputting numerical values is to be increased/improved in safety-relevant applications.

This object is achieved by providing an apparatus for a safety-relevant application. The apparatus has a user interface. The user interface is intended to display a predetermined number of digits. The predetermined number of digits is intended to be filled with numerical values by a user. The user interface is designed to limit a selection of a predetermined number of digits available for a user input when a numerical value is input by the user, for example his/her first input, for one of the digits that are to be filled/are available.

By limiting the option to fill digits with values, the user is proactively prevented from inputting wrong values and, thus, from causing harm.

In particular, user interfaces are understood here for the input of data by a user of a machine. Moreover, the user interface may be the point at which a human interacts with a machine or a device, in this case the apparatus for the safety-relevant application.

The safety-relevant application may be, for example, the administration/infusion of drugs or the like. In general, the safety-relevant application can be understood to be an application in which, in the event of wrong input or wrong operation of the user interface, a human is exposed to direct danger or harm.

The safety aspects of the apparatus for the safety-relevant application can be divided into three categories. Primary safety comprises risks which emanate directly from a system, such as fire caused by a defect in the electronic system. Functional safety comprises dangers that may emanate from the apparatus itself, for example depending on a correct function of the hardware or software of the apparatus. Indirect safety comprises both an indirect effect of errors of the apparatus and defects in the man-machine interface, in this case the user interface. This category also includes non-functional characteristics such as the editing time of a request. Thus, in the present case the safety relevance may primarily relate to the indirect safety as non-functional characteristic of the apparatus.

For comprehension, digits are understood to be places to be filled with values present in the display of the electronic apparatus, viz. the user interface. In this case, the input can be limited to numerical values, i.e., numbers from 0 to 9.

The apparatus may be a medical apparatus. Examples hereof are an infusion pump or a dialysis machine. The safety-relevant application thus is in direct relationship with the human and bears a risk to life and limb.

The user interface of the apparatus can be a touchpad for manual input and output. Furthermore, the user interface can include a mouse for input. The mouse can be used in connection with the touchpad or with a screen having no touch function. Also, the user interface can have or be a touchscreen for manual input/output.

Input of numerical values can be facilitated in this way.

The digits to be filled can be filled separately with numerical values. Equally, the digits to be filled can be filled successively. Note in this context that the digits may be designed so that they can be filled exclusively individually with a respective numerical value by the user.

This helps further reduce the risk of a wrong input.

The user interface can further be configured to distribute the selection of digits available for the user input to an equal number of digits for places before and after the decimal point. The user interface can be configured likewise or additionally to distribute the selection of digits available for the user input to an equal number of digits for a unit and a subunit, preferably hours and minutes or minutes and seconds. Thus, for example, only four digits may be filled with values. When inputting one unit, the adding of a further subunit of a subunit may be blocked. This may also be applicable to the input of a subunit and another subunit so that the upper unit is blocked. In this context, also two places before the decimal point and two places after the decimal point can be filled, for example, but there can be no odd distribution.

Furthermore, the user interface can be configured to shift, by means of the user's input, a decimal point provided on the user interface for the display of places before and after the decimal point between the digits to be filled. For this purpose, the digits after the decimal point may be displayed smaller than the digits before the decimal point. By shifting the decimal point, the user can also make the latter disappear so that, by shifting the decimal point on the display of the user interface, the user selects only digit places before the decimal point.

Also, the touchpad/touchscreen can be configured, when a respective digit to be filled is clicked on by the user, to display a keyboard intended, when a respective numerical value displayed on the keyboard is touched, to fill the respective digit to be filled with said value.

The apparatus may further include a memory. The memory may be intended to store data. The data can comprise at least one hard numerical limit and one soft numerical limit. Said limits can relate to the safety-relevant application. Also, respective hard and soft upper and lower limits with respect to the safety-relevant application can be stored in the memory. The user interface can communicate with the memory. Said communication can be established directly or indirectly via a processing unit or control unit contained in the apparatus. The processing unit or control unit can be configured in accordance with a network, such as a bus, to process data from the memory and the user interface. The user interface can be configured to delay or prevent input progress on the basis of the hard and soft numerical limits. This can be based on an instruction to the user interface provided by the processing unit or control unit.

The user interface can be configured, based on a comparison between at least one of the digits filled with numerical values and the at least one hard numerical limit, to limit a further input or to cancel a previous input. Equally, the user interface can be configured, based on the comparison between the at least one of the digits filled with numerical values and the at least one hard numerical limit, to limit the selection for the user input of available digits and/or a range of numerical values available for selection for the at least one of the available digits. The processing in accordance with the comparison can be performed by the processing unit or control unit.

In this way, the user's attention can be drawn, by appropriate limitations and/or delays, to the apparatus.

In addition, the user interface can be configured, based on a comparison between the at least one of the digits filled with numerical values and the at least one soft limit, to notify that a further input is required. Accordingly, the value in the at least one of the digits filled with numerical values or a total value of all filled digits can be within the at least one hard limit or within a range defined by the hard upper and lower limits, but outside the at least one soft limit or outside a range defined by the soft upper and lower limits.

Consequently, patient safety can be further increased.

Moreover, the above-mentioned object can be achieved by a method for operating an apparatus for a safety-relevant application. The apparatus can correspond to the afore-described apparatus. The method comprises displaying, by a user interface, digits to be filled with numerical values by a user. The method further comprises inputting a numerical value, by a user, for one of the digits to be filled/available. Furthermore, the method comprises limiting, by the user interface, a selection of digits available for a user input on the basis of inputting. In this way, a further input can be limited and/or delayed by inputting a value for one of the displayed digits on the user interface.

Thus, a safety aspect in operating safety-relevant apparatuses can be improved.

In other words, the invention relates to a numerical editor for safety-critical applications on touchscreen user interfaces, for example in the form of a user interface. In particular, the invention relates to an editor concept for touchscreen user interfaces that is intended to minimize the probability of wrong inputs. The input concept used in consumer goods such as smartphones primarily serves for user friendliness rather than for maximum safety. The suggested concept offers a balanced proportion between safety and ergonomics. It can be applied taking a medical infusion pump into consideration which is safety-critical and has a restricted screen size. However, the concept is not limited to infusion pumps. An application in other safety-critical devices in health care and beyond that is imaginable.

In yet other words, the invention may be a technical equipment including a control unit, a connected operating unit and an output unit also connected to the control unit. The operating unit may require a user to input numerical parameters, and the control unit may use said input to generate a desired value for an output unit.

In one or more embodiments, a specific input device, also referred to as editor, which is intended to minimize the probability of wrong inputs of the numerical parameters can be provided in the operating unit.

There may be provided different variants for the technical equipment. For example, the technical equipment may be an apparatus that is intended to carry out, control and/or document one or more safety-critical operations which, in the case of input errors, can result in dangers to humans, goods, the environment and/or financial assets.

In particular, the purpose of the apparatus can be to administer and/or document medical infusions. Moreover, the purpose of the apparatus can be to carry out and/or document dialysis treatments, a therapy using temperature, a therapy using ultrasound, a therapy using electromagnetic radiation (including infrared and X-rays), particle therapy and/or X-ray diagnostics.

Also, the purpose of the apparatus can be the control of a safety-critical operation of a vehicle, an aircraft, a weapon system, industrial plants, business processes, traffic flows, a power plant.

The control unit can be an apparatus comprising a programmable processor including a memory. Said control unit can be additionally provided with a processing logic, for example to carry out infusions or dialysis treatments, which is run on the processor and requires the input of parameters.

The operating unit, at least as part of the user interface, may be an apparatus having a visual output surface and a touch-sensitive input medium provided on said surface. The output surface may display operating elements, wherein the detection of touches can result in triggering specific reactions in the operating unit and the control unit. For this purpose, resistive, capacitive, power-based and/or temperature-based touch sensors can be used. Also, the output surface can be intended to be coupled to the input using a computer mouse or a trackpad, using gesture control and/or using camera-based eye-tracking. The operating unit may be at least part of a tablet or a personal computer.

The output unit may include an actuator/motor carrying out movements according to the set values of the control unit. The actuator can be coupled to a syringe so that an infusion can be administered in a controlled manner. The motor can be coupled to an infusion tube by means of peristalsis so that an infusion can be administered in a controlled manner. Further, the output unit can include a generator of X-rays, electromagnetic waves, particle flows and/or documentation elements.

The numerical parameters in the form of numerical value ranges intended for input can be safety-relevant numerical values such as setting parameters of an infusion therapy (e.g., flow rate, volume to be administered, duration of the infusion, bolus quantity, drug concentration and/or dose rates) or dialysis treatment. Also, the safety-relevant numerical values can be safety-relevant indications of time, energy quantities, performance data and/or velocities.

The users can be heads of safety-critical processes who are required to operate the technical equipment. These include, for example, medical staff (including nursing staff and physicians), hospital technicians, maintenance staff, users of a machine, users of a vehicle and users of a plant.

According to one embodiment, the specific input apparatus, the editor, can be configured as follows. Decimal places of the numerical parameter can be shown so that they are jointly visible but individually selectable on the operating unit. For example, a keyboard with a number line is displayed and activated only when a decimal point is selected by the user. The keyboard may allow setting the value for the selected decimal place. After selecting the value, the keyboard on the operating unit can be hidden and deactivated again. The decimal places located to the right of the edited numerical place can be zero-filled after selection of the value, unless they have been filled already with specific values by the user before. In addition, the keyboard can also include an input element for deleting the value for the selected decimal place. If individual values on the keyboard result in invalid inputs, the associated operating elements are deactivated, for example, and deactivation thereof is indicated to the user (e.g., by greying out).

As an alternative, said values are not displayed on the keyboard at all. In addition, an operating element for deleting/resetting the complete parameter value may be provided. Further, different display sizes for decimal places before and after the decimal point may be provided to prevent confusion of the numerical places. Further operating elements may be provided for shifting the decimal point. Also, no decimal points may be present. An additional display of dependent numerical parameters, too, may be provided during the operating process. Moreover, there may be provided a marking which numerical parameter is concerned (using a parameter name, graphical elements and/or the indication of the technical unit).

Yet another operating element may be provided to confirm the value after completing the input of the numerical parameter by the user. During confirmation, an admissible value range check by the operating and/or control unit can be provided. The check for value ranges conspicuous under safety aspects (soft-limit range) can be carried out by the operating unit and/or control unit during confirmation. A query can be made to the user whether the value is really to be applied, when the value is within the conspicuous value range. Also, the examination result can be output acoustically. The admissible and/or conspicuous value ranges can also be displayed graphically on a number line.

Those skilled in the art are aware of the fact that the explanations given here can be implemented using hardware circuits, software means or a combination thereof. The software means may be in connection with programmed microprocessors or a general computer, an ASIC (Application Specific Integrated Circuit) and/or DSPs (Digital Signal Processors).

For example, the apparatus for the safety-relevant application, the user interface, the memory, the processing unit and the control unit can be partially realized as a computer, a logic circuit, an FPGA (Field Programmable Gate Array), a processor (for example comprising a microprocessor, a microcontroller (μC) or a vector processor)/core (main memory, can be integrated in the processor or can be utilized by the processor)/CPU (Central Processing Unit; plural processor cores being possible), an FPU (Floating Point Unit), an NPU (Numeric Processing Unit), an ALU (Arithmetic Processing Unit), a coprocessor (additional microprocessor for backing up a main processor (CPU)), a GPGPU (General Purpose Computation on Graphics Processing Unit), a parallel computer (for simultaneously performing computing operations, inter alia on plural main processors and/or graphics processors) or a DSP.

Moreover, those skilled in the art are aware of the fact that, even if the details described here are described with respect to a method, said details can also be realized in an appropriate apparatus, a computer processor or a memory connected to a processor, the memory being provided with one or more programs which carry out the method when they are run by the processor. Accordingly, methods such as swapping and paging can be used.

Even if some of the afore-described aspects have been described with respect to the apparatus, said aspects can also be applicable to the method. Likewise, the aspects described above with respect to the method can also be applied mutatis mutandis to the apparatus.

If it reads in the present case that one component "is connected" to, "is communicated" with or "accesses" another component, this can mean that it is directly connected to or directly accesses the same; it is noted in this context, however, that another component may be interposed. If it reads, on the other hand, that one component "is directly connected" to or "directly" accesses another component, it is understood that no further components are present therebetween.

BRIEF DESCRIPTION OF THE DRAWING FIGURES

In the following, the invention will be illustrated by means of drawings, wherein:

FIG. 7 shows a schematic view of an editor with a specified digit;

FIG. 8 shows a schematic view of an editor with limit bars; and

FIG. 9 shows a schematic view of an editor with a soft-limit warning.

The Figures are merely schematic and are solely for the purpose of understanding the invention. Like elements are provided with like reference symbols. The features of the individual embodiments can be interchanged.

Moreover, spatially relative terms such as "located under", "below", "lower", "located above", "upper", "to the left", "left", "to the right", "right" and the like can be used to simply describe the relationship of one element or one structure to one or more other elements or structures shown in the Figures. The spatially relative terms are intended to comprise, in addition to the orientation shown in the Figures, other orientations of the component in use or in operation. The component can be oriented differently (rotated by 90 degrees or in a different orientation), and the spatially relative descriptors used here can likewise be interpreted correspondingly.

DETAILED DESCRIPTION

The method and the apparatus will now be exemplified on the basis of embodiments.

Figure 1:
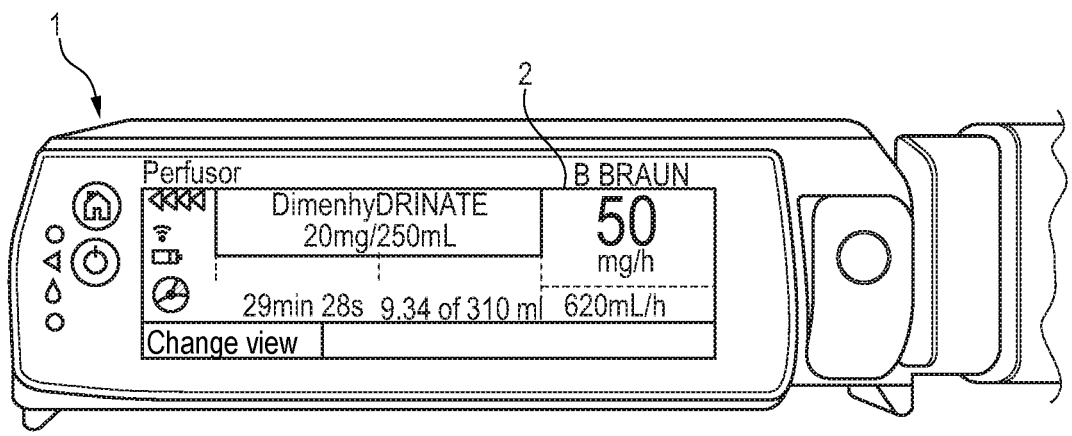
FIG. 1 shows a schematic view of a medical apparatus, viz. an infusion pump, as an example of an apparatus for a safety-relevant application including a graphical display and a touchscreen user interface.

The concept aims at safety-relevant applications, in particular with respect to medical apparatuses, such as the infusion pump 1 having a touchscreen user interface 2 in FIG. 1, in the foregoing also described as user interface 2 or as part thereof, which concept requires numerical data to be input by an operator, also referred to as user.

The editor 3 as interacting tool or input tool for the man-machine operation as part of the above-described user interface 2 is designed with regard to safety. A principle of interaction involves a mechanism forcing the user to maximize his/her attention to the input process when inputting values for an infusion pump 1, for example, as shown in FIG. 1, so as to avoid errors.

The basic idea is to divide a number into number fields 4, referred to as digits here, which must be selected individually and filled with a numerical value by the user. This approach forces the user to reflect on the number during editing, while he/she visually concentrates on the relevant screen elements of the editor 3.

In particular, the number fields 4 are designed interactively.

Figure 2:
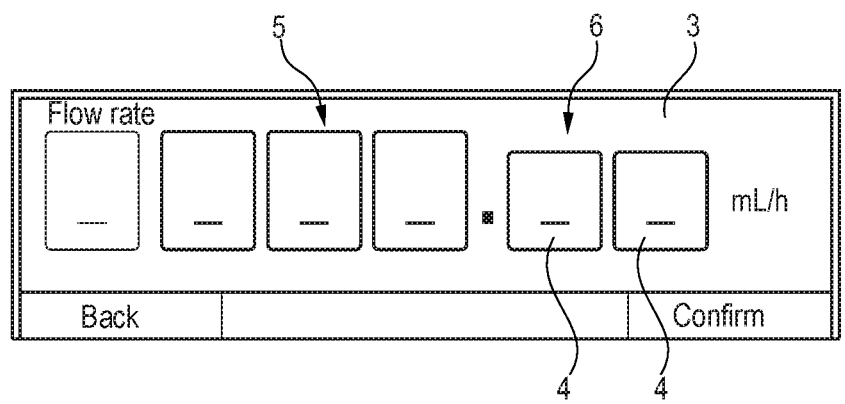
FIG. 2 shows a schematic view of a basic design of an editor.

The editor 3 makes use of a series of number fields 4 allowing to indicate individually number values during programming (see FIG. 2).

The places before the decimal point 5 and the places after the decimal point 6 are separated by a decimal point allowing the user to clearly distinguish the places before the decimal point 5 and the places after the decimal point 6. The places after the decimal point are displayed smaller for further visual distinction. The distance between the number fields 4 may be enlarged to distinguish between hundred digits and thousand digits.

Number fields 4 released for editing may be displayed with a colored, such as white, background, and values can be entered by touching the touchscreen user interface 2 at those places. Number fields 4 which cannot be edited for various reasons (e.g., due to restrictions of limits resulting from apparatus physics or the application) are displayed, for example, with a differently colored background, are greyed out, for example. Therefore, the user can input only values that correspond to specific limits or come within admissible ranges.

The editor 3 as shown in FIG. 2 can display a maximum of six number fields 4, for example. However, the user possibly cannot edit all of the six number fields 4 in which an application logic prevents restricted or illogical values from being indicated. When places after the decimal point 6 are used, the editor 3 can force the user to edit a maximum of four successive number fields 4 so that the user cannot input any illogical value such as "1000.01". Rather, values like "10.25" or "110.5" can be considered as compliant by the application logic. In cases where only places before the decimal point 5 are required to indicate a value, the editor 3 can be displayed also without the decimal point.

Figure 3:
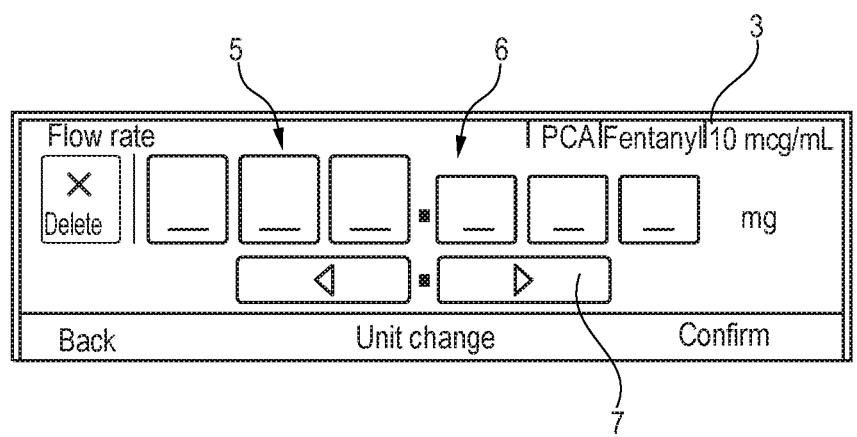
FIG. 3 shows a schematic view of an editor with shiftable decimal point.
Figure 4:
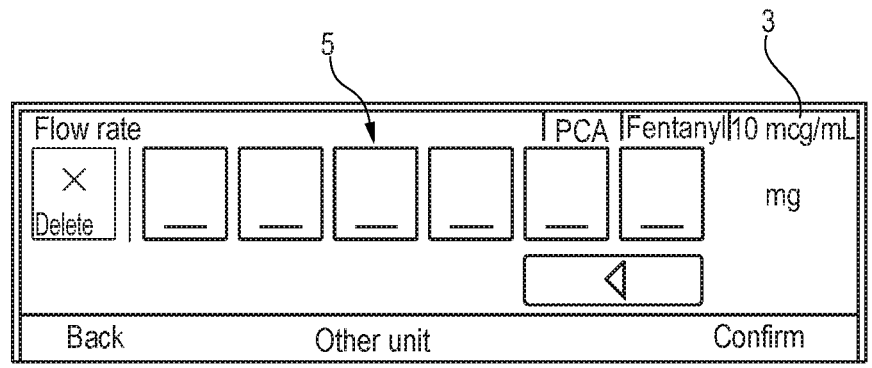
FIG. 4 shows a schematic view of an editor with shifted decimal point (only places before the decimal point)

As schematically shown in FIGS. 3 and 4, the editor 3 may have a movable decimal point. In one application scenario, the decimal point remains at a fixed position and cannot be shifted. However, several scenarios require the flexibility to indicate more or fewer number fields 4 either to the right or to the left of the decimal point (see FIG. 3). In those cases, the editor 3 allows the user to shift the decimal point to a different position via the arrows for moving the decimal point 7. The decimal point can never be shifted without conscious action of the user.

Shifting the decimal point does not change the general function of the editor 3. All additional places after the decimal point 6 and number fields 4 are smaller to ensure the distinction from the places before the decimal point 5. The push buttons 7 for shifting the decimal point likewise move at the position of the decimal point to increase the clarity of the positioning of the decimal point. As soon as a value has been input, the arrows 7 for shifting the decimal point disappear.

Figure 5:
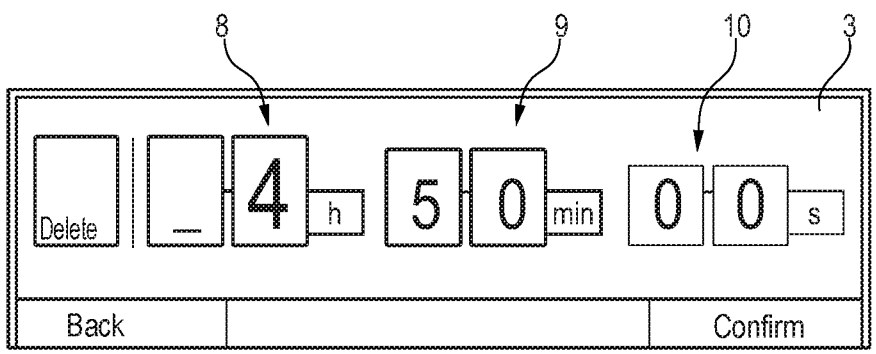
FIG. 5 shows a schematic view of a time editor.

As shown in FIG. 5, an editing of time information can also be provided. Time editors 3 can follow the same scheme and have a division into hours 8 as upper unit, minutes 9 as middle unit and seconds 10 as subunit, irrespective of whether or not they contain editable number fields 4. The simultaneous display of hours 8, minutes 9 and second 10 takes place with the aim of preventing the user from confusing hours 8 with minutes 9 and minutes 9 with seconds 10. If the application logic does not permit the input of hours 8, minutes 9 or seconds 10, the corresponding number fields 4 are highlighted in a different color, for example greyed out (see FIG. 5).

In a possible variant, the user can input optionally either hours 8 in combination with minutes 9 or minutes 9 in combination with seconds 10. When editing initially starts with the input of the number fields 4 for the hours 8, the number fields 4 for the seconds 10 are greyed out and, thus, are no longer available for editing. In this way, the confusion between hours 8, minutes 9 and seconds 10 is reduced.

Selecting a number field 4 or the general concept for use of implementing the numerical editor 3 requires the user to touch initially a specific number field 4 which requires inputting of a numerical value.

Figure 6:
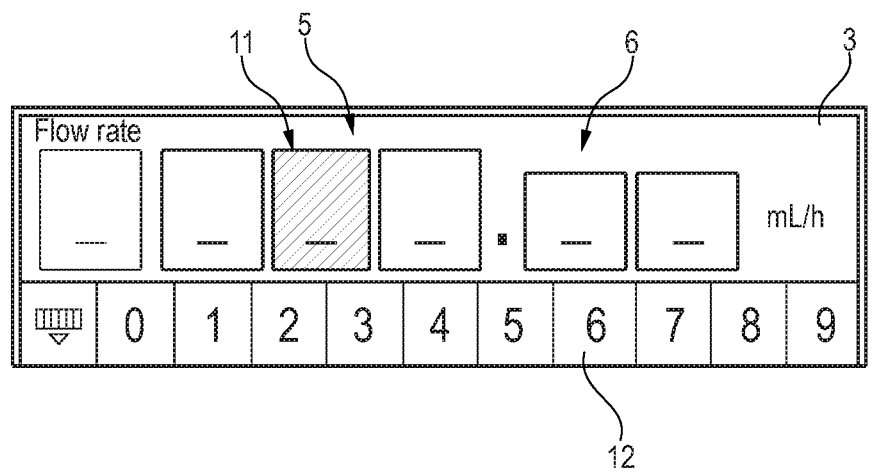
FIG. 6 shows a schematic view of an editor with a selected digit and a numerical keyboard.

When selecting one of the number fields 4 as a selected number field 11, a number block in the form of a (virtual) fold-away/fold-out keyboard 12, which was removed before, appears at the bottom of the editor 3 (see FIG. 6). It indicates all values that can be input at the selected position, namely the selected number field 11. Values which are not allowed to be used at the selected position 11 due to limits or other restrictions, are greyed out on the number block and, thus, are not available.

When the user has input a value for the selected number field 11, the number appears in the number field 11 and the virtual keyboard 12 disappears. The editor 3 fills all places before the decimal point 5 to the right of the indicated place before the decimal point 5 with zeros 13 to avoid the manual input of zeros 13. When the user does not wish to have any zeros 13 for a specific number field 4, he/she can select said number field 4 to change the value thereof. In all cases, the editor 3 fills only number fields 4 in which no hard limits are violated with zeros 13.

The operation for selecting a number field 4 is repeated until the user has indicated the complete value for the desired parameter intended for application.

After the user has set a value, said value must be confirmed by touching the "confirm" key, before the further processing takes place. The selection not to use the indicated value can be made by touching the push button "cancel". In this case, the apparatus, such as the infusion pump 1 of FIG. 1, ignores the changes made by the editor 3 and returns to the previous value (if available) for said parameter.

In order to delete a value in the editor 3 and to restart, the user can touch the push button "delete" 14 which deletes all values of the number fields 4.

The editor 3 contains the concept of the limits which are visually displayed by the so-called limit bar 15. The limit bar 15 is placed above the numerical value in the view shown in FIG. 8.

The limit bar 15 shows at its ends the inadmissible value ranges referred to as hard limits. In the middle area of the bar the standard value range (for example marked in color, grey range) and the soft limit range (for example marked in color, yellow range) are located. The soft limit range marks values, in English frequently referred to as soft limits, which, although admissible, have to be particularly observed/confirmed for safety reasons.

Application-specific limits of an infusion pump 1 can be provided by the drug library which is a collection of drug-related and hospital-related safety information stored in a memory of the infusion pump.

The editor 3 does not allow hard limits to be exceeded as selecting specific number fields 4 or values input to the latter which violate hard limits or correspond to an invalid numerical input will delay or prevent progress in the procedure.

If the user indicates a value that is within the soft limit range for the parameter, the infusion pump 1 reacts by marking the range of the limit bar 15 which is outside the soft limits in a different color, for example yellow (see FIG. 8). A dynamic cursor on the bar indicates where in the range of the possible values the value input by the user is located. This is for the purpose of informing the user before the value is confirmed. For infusion pumps 1 soft limits can be set for a specific drug in the drug library of the apparatus.

If the user confirms a value that is outside a soft limit, the user interface 2 displays a soft limit warning 16 to ensure additional safety. The soft limit warning 16 requests the user to either overwrite the soft-limit warning 16 (i.e., to accept the value) or to return to editing the value so as to change said value (see FIG. 9).

The invention claimed is:

1. A method for operating an apparatus for a safety-relevant application, the method comprising:
    displaying, by a user interface, a predetermined number of fields for receiving an input numerical parameter;
    comparing at least one of the predetermined number of fields to at least one numerical limit or at least one other safety-relevant limitation to determine if the at least one of the predetermined number of fields may receive an input numerical parameter within the at least one numerical limit or at least one other safety-relevant limitation;
    limiting, by the user interface, the predetermined number of fields for receiving the input numerical parameter to a selection of fields that is less than the predetermined number of fields available for a user input of the input numerical parameter based on the comparing; and
    displaying, by the user interface, a numerical value provided by the user based on user selection of one of the selection of fields for receiving the numerical value.

2. An apparatus for a safety-relevant application, the apparatus comprising a user interface that displays a predetermined number of fields for receiving an input numerical parameter, wherein the user interface is configured to limit the predetermined number of fields for receiving the input numerical parameter to a selection of fields that is less than the predetermined number of fields available for a user input of the input numerical parameter based on a comparison between at least one of the predetermined number of fields and at least one numerical limit or at least one other safety relevant limitation and to display a numerical value provided by the user based on user selection of one of the selection of fields for receiving the numerical value.

3. The apparatus according to claim 2, wherein the apparatus is a medical apparatus.

4. The apparatus according to claim 2, wherein the user interface includes a touchpad for manual input/output and/or a mouse for input.

5. The apparatus according to claim 2, wherein the user interface includes a touchscreen for manual input/output.

6. The apparatus according to claim 2, wherein the selection of fields are filled separately and/or successively with numerical values.

7. The apparatus according to claim 2, wherein each of the selection of fields is separately selectable and the user interface is configured, with or by selecting a respective field of said selection of fields, to provide a virtual keyboard generally valid for all of the selection of fields or individually designed or filled for a currently selected field, via which keyboard a numerical value is associated with the currently selected field.

8. The apparatus according to claim 2, wherein the user interface is configured to distribute the selection of the fields to an equal number of fields for places before a decimal point and places after the decimal point or to an equal number of fields for a unit and a subunit.

9. The apparatus according to claim 2, wherein the user interface is configured to shift a decimal point provided on the user interface for displaying places before the decimal point and places after the decimal point between the selection of fields.

10. The apparatus according to claim 2, wherein the selection of fields has fields for places before a decimal point and fields for places after the decimal point, the user interface being configured to zero-fill all places before the decimal point to a right side of input place(s) before the decimal point so as to avoid a manual input of zeros.

11. The apparatus according to claim 2, wherein the apparatus has a memory configured to store data comprising at least one hard numeric limit and/or one soft numeric limit with respect to the safety-relevant application, the user interface communicating with the memory and being configured to delay or prevent an input progress based on the at least one hard numeric limit and/or the at least one soft numeric limit.

12. The apparatus according to claim 11, wherein the user interface is configured to restrict a further input or to reverse a previous input, based on a comparison between at least one of a plurality of numerical values that includes the numerical value for at least one of the selection of fields available for a user input and the at least one hard numeric limit.

13. The apparatus according to claim 11, wherein the user interface is configured to limit a selection of available numerical values for at least one of the selection of fields based on the at least one hard numeric limit.

14. The apparatus according to claim 11, wherein the user interface is configured, based on a comparison between at least one of a plurality of numerical values that includes the numerical value for at least one of the selection of fields and the at least one soft numeric limit, to indicate that a further input is required.

15. A method for operating the apparatus according to claim 2, the method comprising:
    displaying, by the user interface, the predetermined number of fields for receiving the input numerical parameter;

comparing at least one of the predetermined number of fields to at least one numerical limit or at least one other safety-relevant limitation to determine if the at least one of the predetermined number of fields may receive an input numerical parameter within the at least one numerical limit or at least one other safety-relevant limitation;

limiting, by the user interface, the predetermined number of fields for receiving the input numerical parameter to the selection of fields that is less than the predetermined number of fields available for a user input of the input numerical parameter based on the comparing; and displaying, by the user interface, the numerical value provided by the user based on user selection of one of the selection of fields for receiving the numerical value.

16. The apparatus according to claim 2, wherein the user interface further displays a limit bar that shows at its ends inadmissible value ranges of the numerical parameter.

17. The apparatus according to claim 16, wherein the limit bar shows a standard value range in a middle area of the limit bar in a first color and shows a soft limit range in another area of the limit bar in a second color, the soft limit range marking values that are to be confirmed before acceptance.

18. The apparatus according to claim 17, wherein when a user confirms a value that is outside the soft limit range, the user interface displays a soft limit warning that requests the user to either overwrite the soft limit warning or to return to editing the value that is outside the soft limit range.

* * * * *